(12) United States Patent
Duyck et al.

(10) Patent No.: US 7,189,875 B2
(45) Date of Patent: Mar. 13, 2007

(54) DIPHENYLAMINE ALKYLATED WITH OLEFIN MIXTURES CONTAINING FRACTIONS WITH VARYING DEGREES OF ACTIVITY

(75) Inventors: Karl J. Duyck, Waterbury, CT (US); Timothy L. Lambert, Lindenhurst, IL (US)

(73) Assignee: Crompton Corporation, Middlebury, CT (US)

( * ) Notice: Subject to any disclaimer, the term of this patent is extended or adjusted under 35 U.S.C. 154(b) by 589 days.

(21) Appl. No.: 10/815,578

(22) Filed: Mar. 31, 2004

(65) Prior Publication Data

US 2004/0211113 A1    Oct. 28, 2004

Related U.S. Application Data

(60) Provisional application No. 60/459,973, filed on Apr. 4, 2003.

(51) Int. Cl.
 *C07C 211/00* (2006.01)
 *C07C 211/43* (2006.01)

(52) U.S. Cl. .................................... 564/305
(58) Field of Classification Search .......... 564/305
 See application file for complete search history.

(56) References Cited

U.S. PATENT DOCUMENTS

| | | | |
|---|---|---|---|
| 2,943,112 A | 6/1960 | Popoff et al. | 260/576 |
| 3,452,056 A | 6/1969 | Sundholm | 260/390 |
| 3,496,230 A | 2/1970 | Kaplan | 260/576 |
| 4,824,601 A | 4/1989 | Franklin | 252/401 |
| 5,498,809 A | 3/1996 | Emert et al. | 585/13 |
| 5,672,752 A | 9/1997 | Lai et al. | 564/409 |
| 5,750,787 A | 5/1998 | Lai et al. | 564/409 |
| 6,204,412 B1 | 3/2001 | Lai | 564/409 |
| 6,315,925 B1 | 11/2001 | Aebli et al. | 252/401 |
| 6,355,839 B1 | 3/2002 | Onopchenko | 564/409 |

FOREIGN PATENT DOCUMENTS

EP    0387979 A1    9/1999

OTHER PUBLICATIONS

Chuev et al (Toereticheskaa I Eksperimental'naya Khimyiya (1985), 21(3), 321-328).*

* cited by examiner

*Primary Examiner*—Samuel Barts
*Assistant Examiner*—Kellette Gale
(74) *Attorney, Agent, or Firm*—Michael P. Dilworth

(57) ABSTRACT

Disclosed herein is a process for the preparation of alkylated diarylamines comprising adding to said diarylamine an olefin mixture containing highly reactive fractions, as well as fractions exhibiting a relatively lower chemical reactivity, in the presence of an acidic clay catalyst at a temperature low enough to prevent substantial deactivation of the catalyst until the addition is complete and then increasing the temperature to increase the alkylation rate of the less reactive fractions.

9 Claims, 2 Drawing Sheets

US 7,189,875 B2

DIPHENYLAMINE ALKYLATED WITH OLEFIN MIXTURES CONTAINING FRACTIONS WITH VARYING DEGREES OF ACTIVITY

I claim the benefit under Title 35, United States Code, § 120 to U.S. Provisional Application No. 60/459,973, filed Apr. 4, 2003, entitled DIPHENYLAMINE ALKYLATED WITH OLEFIN MIXTURES CONTAINING FRACTIONS WITH VARYING DEGREES OF ACTIVITY.

BACKGROUND OF THE INVENTION

1. Field of the Invention

The present invention relates to a mixture of alkylated diphenylamines, to a process for the preparation of that mixture, and to the use thereof as an additive for stabilizing organic products that are subjected to oxidative, thermal, and/or light-induced degradation. The additives can be added to numerous organic products widely used in engineering, for example, lubricants, hydraulic fluids, metalworking fluids, fuels, or polymers, to improve their performance properties.

2. Description of Related Art

U.S. Pat. No. 2,943,112 describes anti-oxidants from the group of the alkylated diphenylamines that are prepared by reaction of diphenylamine with alkenes in the presence of mineral acids and large quantities of acid clays as catalysts. Alkylation of the diphenylamine with alkenes results in mixtures of mono- and di-alkylated diphenylamine. In that process, relatively large quantities of the starting material, generally from 6 to 12% diphenylamine, are not reacted, which reduces the anti-oxidative efficacy of the alkylated diphenylamines, leads to the deposition of sludge, and imparts undesirable toxic properties to the product. Reaction with additional alkenes is proposed as an alternative to the distillative separation of the starting material from the products.

U.S. Pat. No. 3,496,230 describes the preparation of a mixture of 80% dinonyldiphenylamine and 15% nonyldiphenylamine in the presence of Friedel-Crafts catalysts of the aluminum chloride type, but that mixture still has a diphenylamine content of 2% (see Example 2 of the patent). As has been shown in U.S. Pat. No. 6,315,925, the preparation of that mixture is especially disadvantageous since it is contaminated by traces of chlorine, metal compounds, and undesirable by-products, e.g. N-alkylated diphenylamines and diphenylamines alkylated in the 2- and 2'-positions, is black in color, and is very viscous.

U.S. Pat. No. 4,824,601 discloses a process for the production of a liquid antioxidant composition by reaction of diphenylamine with diisobutylene comprising reacting diphenylamine with diisobutylene in a molar ratio of from 1:1.1 to 1:2.5 and in the presence of an acid activated earth catalyst, while ensuring that the concentration of diisobutylene remains substantially constant throughout the reaction period at a reaction temperature of at least 160° C., the reaction being effected for such a period that the content of 4,4'-dioctyldiphenylamine in the reaction mass, excluding catalyst, is below 25% by weight; and removing catalyst and unreacted diisobutylene. The use of this product as a stabilizer for organic material against oxidative degradation is also disclosed.

U.S. Pat. No. 6,315,925 discloses a mixture of nonylated diphenylamines, especially dinonylated diphenylamines, and a technically advantageous methodological process for the preparation of that mixture by using acid catalysts in small quantities. The mixture is used as an additive for stabilizing organic products that are subjected to oxidative, thermal, and/or light-induced degradation.

U.S. Pat. No. 6,355,839 discloses a process for the preparation of alkylated diphenylamine antioxidants that comprises alkylating diphenylamine with a polyisobutylene in the presence of a clay catalyst, wherein the polyisobutylene has an average molecular weight in the range of 120 to 600 and wherein the polyisobutylene contains at least 25% methylvinylidene isomer.

The disclosures of the foregoing are incorporated herein by reference in their entirety.

SUMMARY OF THE INVENTION

It is an object of this invention to provide a novel mixture of diphenylamines alkylated with isobutylene oligomers and/or propylene oligomers.

It is another object of this invention to provide a novel process for obtaining the novel mixture.

It is another object to provide an improved process for alkylating diphenylamine with mixtures of olefins having fractions that are more reactive relative to the other fractions of the mixture.

It is still another object to provide the mixture as a lubricant additive effective for imparting antioxidant properties to a lubricating oil, fuel composition, or rubber formulation.

These and other objects are achieved by the present invention, which is related to a process for the preparation of lubricant additives that are derived from the alkylation of a diarylamine, preferably diphenylamine, by adding to said diarylamine olefin mixtures containing highly reactive fractions, as well as fractions exhibiting a relatively lower chemical reactivity, in the presence of an acidic clay catalyst at a temperature low enough to prevent substantial deactivation of the catalyst until the addition is complete and then increasing the temperature to increase the alkylation rate of the less reactive fractions. The alkylated diphenylamines are defined by the general formula:

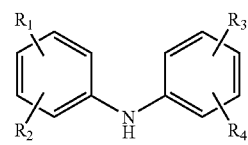

wherein $R_1$, $R_2$, $R_3$, and $R_4$ are independently selected from the group consisting of hydrogen, oligomers of isobutylene, and oligomers of propylene, provided that at least one of $R_1$, $R_2$, $R_3$, and $R_4$ is not hydrogen.

This process produces a mixture of diarylamines, e.g., diphenylamines, that have been alkylated with oligomers of isobutylene or oligomers of propylene that are shown to have beneficial performance and physical properties.

More particularly, the present invention is directed to a process for producing alkylated diphenylamines of the general formula:

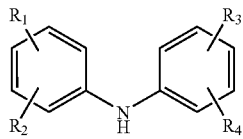

wherein $R_1$, $R_2$, $R_3$, and $R_4$ are independently selected from the group consisting of hydrogen, oligomers of isobutylene, and oligomers of propylene, provided that at least one of $R_1$, $R_2$, $R_3$, and $R_4$ is not hydrogen, wherein the process comprises adding to a diphenylamine a mixture of oligomers of isobutylene or a mixture of oligomers of propylene in which said mixtures comprise highly reactive fractions, as well as fractions having lesser reactivity, in the presence of an acidic clay catalyst at a temperature low enough to prevent substantial deactivation of the catalyst until the addition is complete and then increasing the temperature to increase the alkylation rate of the less reactive fractions.

In another aspect, the present invention is directed to an alkylated diphenylamine of the general formula:

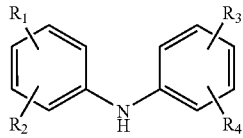

wherein $R_1$, $R_2$, $R_3$, and $R_4$ are independently selected from the group consisting of hydrogen, oligomers of isobutylene, and oligomers of propylene, provided that at least one of $R_1$, $R_2$, $R_3$, and $R_4$ is not hydrogen, prepared by a process comprising adding to a diphenylamine a mixture of oligomers of isobutylene or a mixture of oligomers of propylene in which said mixtures comprise highly reactive fractions, as well as fractions having lesser reactivity, in the presence of an acidic clay catalyst at a temperature low enough to prevent substantial deactivation of the catalyst until the addition is complete and then increasing the temperature to increase the alkylation rate of the less reactive fractions.

In still another aspect, the present invention is directed to a composition comprising:

A) an organic product selected from the group consisting of lubricants, hydraulic fluids, metal-working fluids, fuels, and polymers; and B) a stabilizing amount of an alkylated diphenylamine of the general formula:

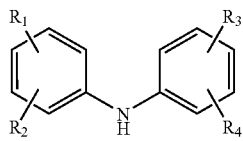

wherein $R_1$, $R_2$, $R_3$, and $R_4$ are independently selected from the group consisting of hydrogen, oligomers of isobutylene, and oligomers of propylene, provided that at least one of $R_1$, $R_2$, $R_3$, and $R_4$ is not hydrogen, prepared by a process comprising adding to a diphenylamine a mixture of oligomers of isobutylene or a mixture of oligomers of propylene in which said mixtures comprise highly reactive fractions, as well as fractions having lesser reactivity, in the presence of an acidic clay catalyst at a temperature low enough to prevent substantial deactivation of the catalyst until the addition is complete and then increasing the temperature to increase the alkylation rate of the less reactive fractions.

In a preferred embodiment, $R_1$ is isobutyl, diisobutyl, triisobutyl, tetraisobutyl, pentaisobutyl, hexaisobutyl, heptaisobutyl, or other polyisobutyl group, or an oligomer of propylene, and $R_2$, $R_3$, and $R_4$ are independently selected from the group consisting of hydrogen, isobutyl, diisobutyl, triisobutyl, tetraisobutyl, pentaisobutyl, hexaisobutyl, heptaisobutyl, or other polyisobutyl, or an oligomer of propylene.

Such compounds may be useful as antioxidants in compounded tires, polyols, plastics, urethanes, greases, motor oils, rubber belts, cables, gaskets, seals, and rubber products in the garment and carpet industries.

DESCRIPTION OF THE PREFERRED EMBODIMENTS

One olefin mixture employed in the practice of this invention is a distribution of isobutylene oligomers:

$$\sum_{n=2}^{8} C_{4n}$$

Diisobutylene (DIB, n=2) reacts at or near the mass transfer controlled rate over the temperature range 130° C. to 160° C. while the higher (n>2) oligomers do not. Since DIB reacts faster than the other oligomers, the oligomer distribution is deficient in $C_8$ in the reaction pot relative to the feed distribution. This means the oligomer distribution during a semi-continuous addition can be used as a gauge of the catalyst activity as a function of time during a reaction, since if the catalyst activity changes by deactivation during the addition, the $C_8$ component of the distribution will increase as a function of time.

Figure 1:
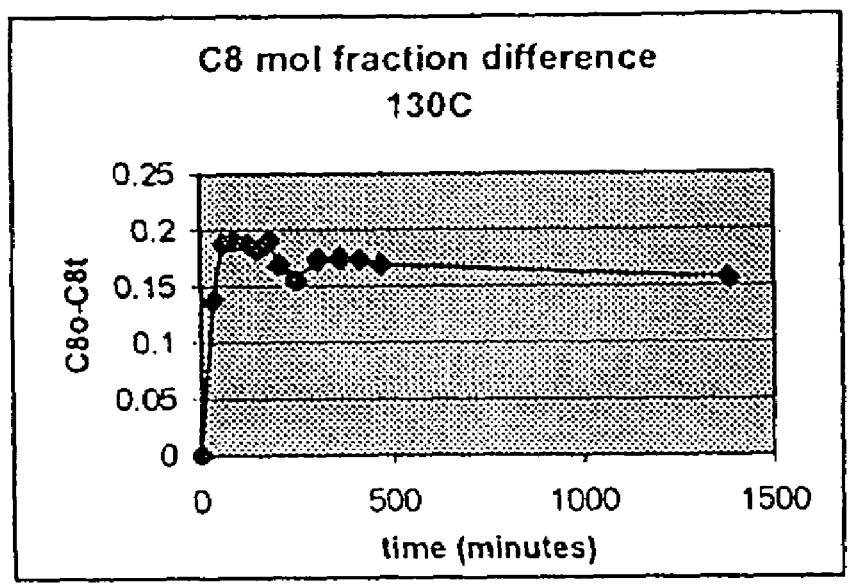
FIG. 1 is a graph showing the $\Delta$ in mole percent DIB for the feed minus the measured mole percent DIB as a function of reaction time at a reaction temperature of 130° C.
Figure 2:
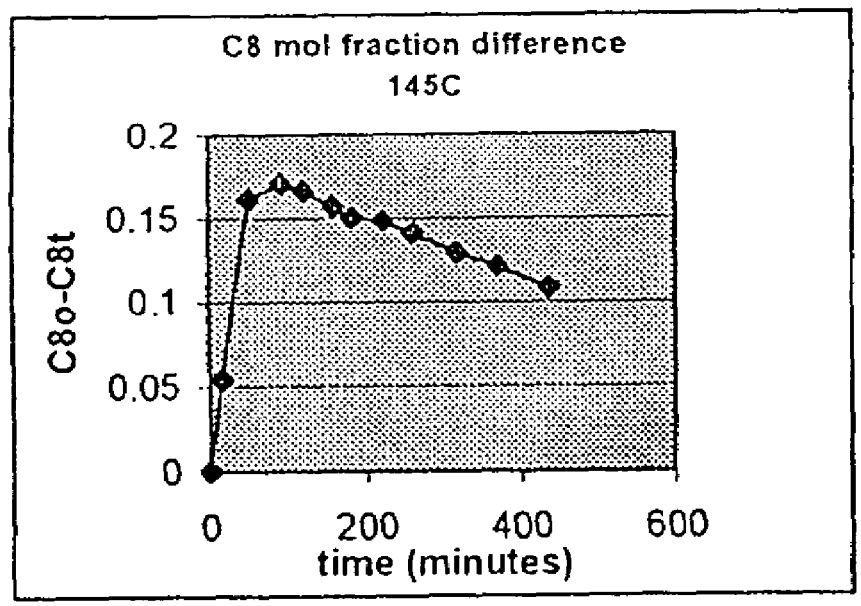
FIG. 2 is a graph showing the $\Delta$ in mole percent DIB for the feed minus the measured mole percent DIB as a function of reaction time at a reaction temperature of 145° C.
Figure 3:
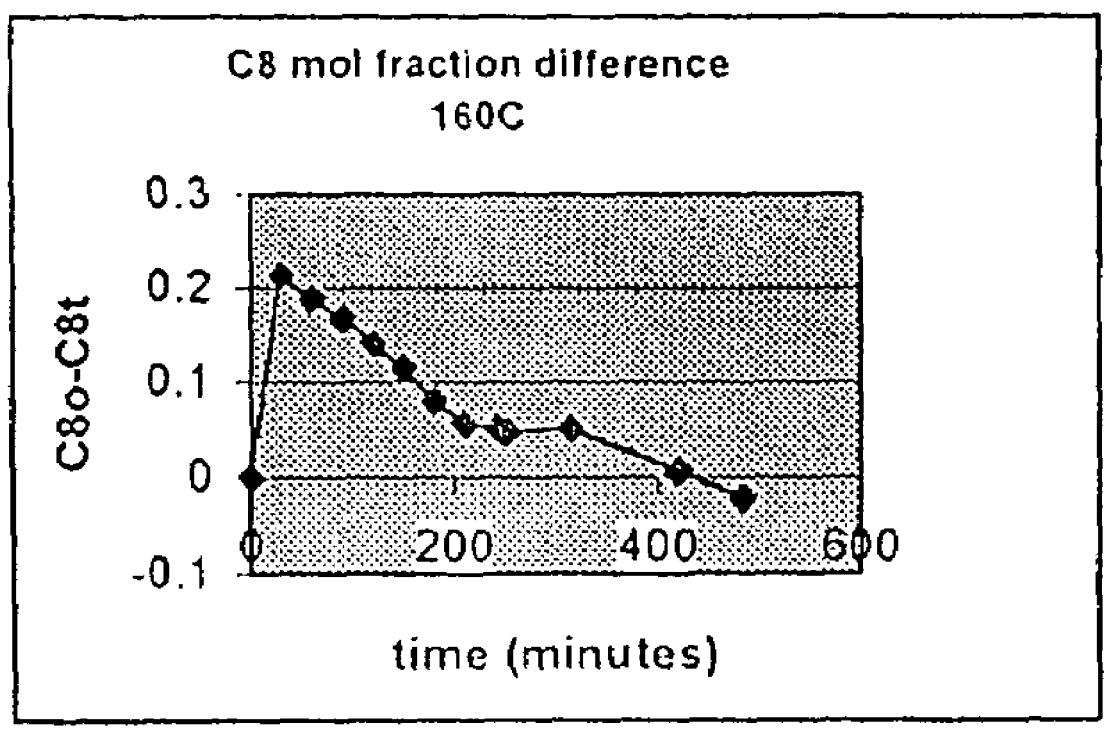
FIG. 3 is a graph showing the $\Delta$ in mole percent DIB for the feed minus the measured mole percent DIB as a function of reaction time at a reaction temperature of 160° C.

FIGS. 1, 2, and 3 are three graphs showing the delta ($\Delta$) in mole percent DIB for the feed minus the measured mole percent DIB as a function of reaction time at reaction temperatures of 130° C., 145° C., and 160° C., respectively. At 130° C., the $\Delta$ remains relatively constant and shows no correlation with reaction time. At 145° C., the $\Delta$ does correlate with reaction time, with the $\Delta$ decreasing at longer reaction times. At 160° C., the same effect is observed as at 145° C., but to a much greater degree. The explanation for this behavior is that the catalyst deactivates and the deactivation is temperature dependent. Thus, it deactivates rapidly at 160° C., less so at 145° C., and practically not at all at 130° C.

To summarize for the isobutylene example,
1) The $C_8$ reacts at the mass transfer controlled rate over the temperature range studied.
2) The temperature dependence of the rate of mass transfer limited reactions is small ($E_{act}$'s in the neighborhood of 5 kcal/mol).
3) The catalyst deactivation rate is strongly temperature dependent.

Similarly, for mixtures that are oligomers of propylene:
1) The alpha olefin fractions in the mixture will be consumed at a higher rate relative to the rate for other propylene oligomers with internal double-bonds.
2) Catalyst deactivation rate is strongly temperature dependent.

For both distributions of oligomers, all highly reactive fractions are consumed while the catalyst is fresh, then (at elevated temperatures) the less reactive fractions are left to react under conditions where the catalyst's effectiveness has been significantly diminished.

According to the present invention, the reaction conditions are arranged so that, during addition of the olefin mixture, catalyst deactivation is kept to a minimum and the reaction rate for the highly reactive fraction is at or near the rate of mass transfer. Once the addition is complete, reaction conditions can be altered (i.e., raising the temperature) to increase the alkylation rate for the other fractions. In this way, one gains most of the benefit of the rapid alkylation rate of the highly reactive fraction while prolonging the catalyst deactivation and thereby improving the overall reaction rate. Through this process, very high conversions of the DPA, to <1% residual can be obtained in a shorter period of time.

Additionally, oligomers of isobutylene are known to undergo "cracking", a process whereby one or more units of isobutylene break away from the oligomer chain. This occurs under acidic conditions at elevated temperatures. In any process for alkylating diphenylamine with oligomers of isobutylene, isobutylene will invariably be produced, which may participate in alkylation to produce tert-butyl diphenylamine and di-tert-butyl diphenylamine, both of which can have a negative impact on product and/or performance characteristics. By using the process of the present invention, these two species can be limited in the finished material. Further, since the oligomers of isobutylene react slowly and "cracking" is only a significant factor at elevated temperatures, the average chain length of the alkylated material can be controlled by consuming the most reactive fractions at a low temperature and then raising the temperature to increase the rate of both cracking (thus shortening chain length in the olefins that have yet to react) and alkylation of the less reactive fractions.

Through the above process the molecular weight distribution of the product can be manipulated and narrowed to a more advantageous composition as described. Most beneficial is a mixture comprised of 0.1 to 1% diphenylamine (DPA), <10% tert-butyl DPA, <10% di-tert-butyl DPA, <10% mono-octyl DPA, >20% dodecyl DPA, >15% hexadecyl DPA, <10% eicosenyl DPA, <7% tetracosenyl DPA, <4% octacosenyl DPA and <2% polyisobutyl DPA. Additionally, not more that 27% of the total reaction mixture can be comprised of $C_8$ alkylation or less, and no more than 15% of the total reaction mixture can be comprised of $C_{24}$ alkylation or more. This mixture may also contain up to about 5% unreacted olefin once stripping has been completed.

In addition to diphenylamine, other aromatic amines are subject to alkylation by the process of the present invention. Such other aromatic amines include, for example: N-phenyl-1-naphthylamine, N-phenyl-2-naphthylamine, p,p'-phenylenediamine, phenothiazine, phenoxazine, p-aminodiphenylamine, p-methylamino-diphenylamine, and p-isopropylarnino-diphenylamine.

Thus, the present invention provides an alkylated diphenylamine that is an effective antioxidant by a process comprising alkylating diphenylamine with an isobutylene or propylene oligomer under suitable alkylation reaction conditions in the presence of an acidic clay alkylation catalyst.

Generally, the isobutylene oligomer will have a number average molecular weight of about 120 to about 600, preferably in the range of about 150 to about 400, and more preferably in the range of about 160 to about 280 and a methylvinylidene content of at least about 25%, preferably in the range of about 25% to about 95%, more preferably in the range of about 40% to about 95%, and even more preferably in the range of about 60% to about 90%. Diisobutylene ($C_8$) may be present in the polyisobutylene in a fractional amount ranging from 0% to about 50% and preferably from about 10% to about 50%.

The use of clay as catalyst in the alkylation of diphenylamine is disclosed in U.S. Pat. No. 3,452,056, which describes the alkylation of diphenylamine with alpha-methylstyrene and related olefins using clay as the catalyst. In U.S. Pat. No. 2,943,112 and elsewhere, clay is described as having several advantages including, for example: (1) it provides a lighter colored product, (2) it can easily be removed by filtration after the reaction, and (3) it provides a lower degree of yellow color in the alkylated product. As a catalyst, clay and other Lewis Acids, such as $AlCl_3$ or $BF_3$ are generally taught as being interchangeable. (See, U.S. Pat. Nos. 3,452,056 and 5,672,752). More recently, U.S. Pat. Nos. 5,672,752; 5,750,787; and 6,204,412 identify certain commercially available clay catalysts, including; Filtrol™ and Retrol™ available from Engelhard; Fulcat™ 14, Fulmont™ 700C, Fulmont™ 237, and Fulcat™ 22B available from Laporte Industries; and Katalysator™ K10 available from Sud-Chemi. These clays may include acid activated or acid leached clays. The clay catalysts may contain some water as received. Removal of the water prior to use results in a lighter colored reaction product. Therefore, it is desirable to use clay with low water content or remove the water by heating the clay with a nitrogen sweep or with vacuum stripping. Acid activated clays are preferred; however, Lewis Acids such as $AlCl_3$ or $BF_3$, and $BF_3$ complexes of diethyl ether, phenol, including mixtures thereof with clay could be used if special circumstances warranted.

The present invention also relates to stabilizer-containing compositions comprising organic products subject to oxidative, thermal, and/or light-induced degradation and, as stabilizer, the mixture of alkylated diphenylamines as defined above and prepared according to the process of the invention.

A particular class of organic products subject to undesirable oxidative degradation for which the mixtures of the present invention are valuable stabilizers is formed by lubricants and operational fluids based on mineral oil or synthetic lubricants or operational fluids, e.g., carboxylic acid ester derivatives, that can be used at temperatures of 200° C. and above.

The mixtures of the present invention can be used in concentrations of from about 0.05 to about 10.0% by weight, based on the material to be stabilized. Preferred concentrations are from 0.05 to 5.0% by weight, especially from 0.1 to 2.5% by weight.

Mineral and synthetic lubricating oils, lubricating greases, hydraulic fluids, and elastomers improved in this manner exhibit excellent anti-oxidation properties which become apparent through a great reduction in the ageing phenomena exhibited by the parts being protected. The mixtures described above are especially advantageous in lubricating oils, in which they exhibit an excellent anti-oxidation and anti-corrosion action without the formation of acid or sludge.

Examples of synthetic lubricating oils include lubricants based on: a diester of a diprotonic acid with a monohydric alcohol, e.g. dioctyl sebacate or dinonyl adipate; a triester of trimethylolpropane with a monoprotonic acid or a mixture of such acids, e.g., trimethylolpropane tripelargonate or tricaprylate or mixtures thereof; a tetraester of pentaerythritol with a monoprotonic acid or a mixture of such acids, e.g. pentaerythritol tetracaprylate; or a complex ester of monoprotonic or diprotonic acids with polyhydric alcohols, e.g., a complex ester of trimethylolpropane with caprylic and sebacic acid or of a mixture thereof.

Other synthetic lubricants are familiar to those skilled in the art and are described, for example, in "Schmiermittel Taschenbuch" (Huthig-Verlag, Heidelberg, 1974). Especially suitable, for example, are poly-α-olefins, ester-based lubricants, phosphates, glycols, polyglycols, and polyalkylene glycols.

Suitable elastomers are familiar to the person skilled in the art. Especially suitable are natural and synthetic rubbers, for example, polymers of butadiene and copolymers thereof with styrene or acrylonitrile, and isoprene or chloroprene polymers.

Another class of polymers to be protected is formed by polycondensates, which can be protected from oxidative and light-induced degradation both in the state of the condensed macromolecular end product and in the state of the low molecular weight starting materials by the addition of the mixtures described hereinbefore. This class includes especially the polyurethanes, which can be stabilized by the addition of dinonyldiphenylamines to, for example, the polyols on which they are based.

The mixtures of the present invention can also be added to natural and synthetic organic substances that are pure monomeric compounds or mixtures thereof, for example, mineral oils, animal or vegetable oils, waxes, and fats, or oils, waxes, and fats based on synthetic esters, e.g., phthalates, adipates, phosphates, or trimellitates, and blends of synthetic esters with mineral oils in any desired weight ratios, as are used, for example, as spinning preparations, and aqueous emulsions thereof.

The mixtures of the present invention can be added to natural and synthetic emulsions of natural or synthetic rubbers, e.g., natural rubber latex or latexes of carboxylated styrene/butadiene copolymers.

The additives derived from this invention can be used as a complete or partial replacement for commercially available antioxidants currently used in lubricant formulations. The additives of this invention can be used in combination with other additives typically found in lubricating oils, and such combinations may, in fact, provide synergistic effects toward improving desired properties, such as improved deposit control, anti-wear, frictional, antioxidant, low temperature, and like properties, to the lubricating oil. The typical additives found in motor oils and fuels are dispersants, detergents, rust inhibitors, antioxidants, anti-wear agents, anti-foamants, friction modifiers, seal swell agents, demulsifiers, viscosity index (VI) improvers, and pour point depressants. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like. Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of antioxidants include alkylated diphenylamines, N-alkylated phenylenediamines, phenyl-α-naphthylamine, alkylated phenyl-α-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. The following are exemplary of such additives and are commercially available from Crompton Corporation: Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, and Naugalube 420, among others.

Examples of anti-wear additives that can be used in combination with the additives of the present invention include organo-borates, organo-phosphites, organo-phosphates, organic sulfur-containing compounds, sulfurized olefins, sulfurized fatty acid derivatives (esters), chlorinated paraffins, zinc dialkyldithiophosphates, zinc diaryldithiophosphates, phosphosulfurized hydrocarbons, and the like. The following are exemplary of such additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. The following are exemplary of such additives and are commercially available from R. T. Vanderbilt Company, Inc.: Molyvan A, Molyvan L, Molyvan 807, Molyvan 856B, Molyvan 822, Molyvan 855, among others. The following are also exemplary of such additives and are commercially available from Asahi Denka Kogyo K. K.: SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, among others. The following are also exemplary of such additives and are commercially available from Akzo Nobel Chemicals GmbH: Ketjen-Ox 77M, Ketjen-Ox 77TS, among others.

An example of an anti-foamant is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

As noted above, suitable anti-wear compounds include dialkyl dithiophosphates. Preferably, the alkyl groups contain an average of at least 3 carbon atoms. Particularly useful are metal salts of at least one dihydrocarbyl dithiophosphoric acid wherein the alkyl groups contain an average of at least 3 carbon atoms.

Lubricant Compositions

Compositions, when they contain these additives, are typically blended into a base oil in amounts such that the additives therein are effective to provide their normal attendant functions. Representative effective amounts of such additives are illustrated in the following table.

| Additives | Preferred Weight % | More Preferred Weight % |
|---|---|---|
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 0.1–10 | 0.1–5 |
| Lube Oil Flow Improver | 0.01–2 | 0.01–1.5 |
| Detergent/Rust Inhibitor | 0.01–6 | 0.01–3 |
| Pour Point Depressant | 0.01–1.5 | 0.01–0.5 |
| Anti-foaming Agents | 0.001–0.1 | 0.001–0.01 |
| Anti-wear Agents | 0.001–5 | 0.001–1.5 |
| Seal Swell Agents | 0.1–8 | 0.1–4 |
| Friction Modifiers | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention, together with one or more of the other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil base stocks. The lubricating oil base stock is any natural or synthetic lubricating oil base stock fraction having a kinematic viscosity at 100° C. of about 2 to about 200 cSt, more preferably about 3 to about 150 cSt, and most preferably about 3 to about 100 cSt. The lubricating oil base stock can be derived from natural lubricating oils, synthetic lubricating oils, or mixtures thereof Suitable lubricating oil base stocks include base stocks obtained by isomerization of synthetic wax and wax, as well as hydrocracked base stocks produced by hydrocracking (rather than solvent extracting) the aromatic and polar components of the crude. Natural lubricating oils include animal oils, such as lard oil, vegetable oils (e.g., canola oils, castor oils, sunflower oils), petroleum oils, mineral oils, and oils derived from coal or shale.

Synthetic oils include hydrocarbon oils and halo-substituted hydrocarbon oils, such as polymerized and interpolymerized olefins, gas-to-liquids prepared by Fischer-Tropsch technology, alkylbenzenes, polyphenyls, alkylated diphenyl ethers, alkylated diphenyl sulfides, as well as their derivatives, analogs, homologs, and the like. Synthetic lubricating oils also include alkylene oxide polymers, interpolymers, copolymers, and derivatives thereof, wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Other esters useful as synthetic oils include those made from copolymers of α-olefins and dicarboxylic acids which are esterified with short or medium chain length alcohols. The following are exemplary of such additives and are commercially available from Akzo Nobel Chemicals SpA: Ketjenlubes 115, 135, 165, 1300, 2300, 2700, 305, 445, 502, 522, and 6300, among others.

Silicon-based oils, such as the polyalkyl-, polyaryl-, polyalkoxy-, or polyaryloxy-siloxane oils and silicate oils, comprise another useful class of synthetic lubricating oils. Other synthetic lubricating oils include liquid esters of phosphorus-containing acids, polymeric tetrahydrofurans, poly α-olefins, and the like.

The lubricating oil may be derived from unrefined, refined, re-refined oils, or mixtures thereof Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Re-refined oils are obtained by treating refined oils in processes similar to those used to obtain the refined oils. These re-refined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a VI of at least 130, preferably at least 135 or higher and, following dewaxing, a pour point of about −20° C. or lower.

The additives of the present invention are especially useful as components in many different lubricating oil compositions. The additives can be included in a variety of oils with lubricating viscosity, including natural and synthetic lubricating oils and mixtures thereof The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions and in rubber formulations.

The advantages and the important features of the present invention will be more apparent from the following examples.

EXAMPLES

Example 1

One hundred and fifty grams (0.89 mol) of diphenylamine was heated to 60° C. To this was added 45 grams of Filtrol 20× and the mixture was heated to 130° C. PIB distillate (382.5 grams) was then charged over 4.167 hours. Once all reactants were added, the reaction mass was held at temperature for 18 hours. The catalyst was removed and the residual starting materials were stripped off under vacuum.

Example 2

One hundred and fifty grams (0.89 mol) of diphenylamine was heated to 60° C. To this was added 45 grams of Filtrol 20× and the mixture was heated to 145° C. PIB distillate (382.5 grams) was then charged over 5.917 hours. Once all reactants were added, the reaction mass was held at temperature for 16 hours. The catalyst was removed and the residual starting materials were stripped off under vacuum.

Example 3

One hundred and fifty grams (0.89 mol) of diphenylamine was heated to 60° C. To this was added 45 grams of Filtrol 20× and the mixture was heated to 160° C. PIB distillate (382.5 grams) was then charged over 4.217 hours. Once all reactants were added, the reaction mass was held at temperature for 4 hours. The catalyst was removed and the residual starting materials were stripped off under vacuum.

Example 4

One hundred and fifty grams (0.89 mol) of diphenylamine was heated to 60° C. To this was added 45 grams of Filtrol 20× and the mixture was heated to 130° C. PIB distillate (382.5 grams) was then charged at a rate sufficient to maintain the reaction temperature. Once all reactants were added, the temperature was raised to 150° C. and held there for 12 hours. The catalyst was removed and the residual starting materials were stripped off under vacuum.

Oxidation Test

Pressure Differential Scanning Calorimetry Test

The antioxidant properties of the reaction products were determined in the Pressure Differential Scanning Calorimetry (PDSC) Test. Testing was performed using the Mettler-Toledo DSC27HP tester, following outlined procedures. This test measures the relative Oxidation Induction Time (OIT) of antioxidants in lubricating fluids as measured in $O_2$ gas under pressure.

The samples to be tested were blended into a model fully-formulated motor oil (see Table 1) that did not contain antioxidant, at 0.4% by weight. An additional 0.1 wt.% of Solvent Neutral 150 base oil was then added along with 50 ppm ferric naphthenate. These were then compared to a sample of the base blend containing 0.5 wt.% of Solvent Neutral 150 base oil and 50 ppm ferric naphthenate. The conditions for the test are shown in Table 2. In Table 3, the numerical value of the test results (OIT, minutes) increases with an increase in effectiveness.

TABLE 1

| Base Blend for PDSC Test | |
| --- | --- |
| Component | Weight Percent |
| Solvent Neutral 150 | 83.85 |
| Zinc Dialkyldithiophosphate | 1.01 |
| Succinimide Dispersant | 7.58 |
| Overbased Calcium Sulfonate Detergent | 1.31 |
| Neutral Calcium Sulfonate Detergent | 0.5 |
| Antioxidant | 0.0 |
| Rust Inhibitor | 0.1 |
| Pour Point Depressant | 0.1 |
| OCP VI Improver | 5.55 |

TABLE 2

| PDSC Conditions | |
| --- | --- |
| Conditions | Setting |
| Temperature | 200° C. |
| Gas | Oxygen |
| Flow Rate | 100 mL/minute |
| Pressure | 500 psi |
| Sample Size | 1–5 mg |
| Pan (open/closed) | open |

TABLE 3

| PDSC Results | |
| --- | --- |
| Compound | OIT |
| Base Blend | 5.45 |
| Example 1 | 17.03 |

TABLE 3-continued

PDSC Results

| Compound | OIT |
|---|---|
| Example 2 | 18.74 |
| Example 3 | 18.48 |
| Example 4 | 18.21 |

TABLE 4

Viscosity, as measured by ASTM D445 at 40° C.

| Compound | Viscosity |
|---|---|
| Example 1 | 1082 |
| Example 2 | 1300 |
| Example 3 | 1244 |
| Example 4 | 1050 |

In view of the many changes and modifications that can be made without departing from principles underlying the invention, reference should be made to the appended claims for an understanding of the scope of the protection to be afforded the invention.

What is claimed is:

1. An alkylated diphenylamine of the general formula:

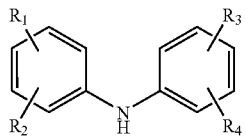

wherein $R_1$, $R_2$, $R_3$, and $R_4$ are independently selected from the group consisting of hydrogen, oligomers of isobutylene, and oligomers of propylene, provided that at least one of $R_1$, $R_2$, $R_3$, and $R_4$ is not hydrogen, prepared by a process comprising adding to a diphenylamine a mixture of oligomers of isobutylene or a mixture of oligomers of propylene in which said mixtures comprise highly reactive fractions, as well as fractions having lesser reactivity, in the presence of an acidic clay catalyst at a temperature low enough to prevent substantial deactivation of the catalyst until the addition is complete and then increasing the temperature to increase the alkylation rate of the less reactive fractions to yield a product that comprises 0.1 to 1% diphenylamine, <10% tert-butyl diphenylamine, <10% di-tert-butyl diphenylamine, <10% mono-octyl diphenylamine, >20% dodecyl diphenylamine, >15% hexadecyl diphenylamine, <10% eicosenyl diphenylamine, <7% tetracosenyl diphenylamine, <4% octacosenyl diphenylamine and <2% polyisobutyl diphenylamine.

2. The alkylated diphenylamine of claim 1 wherein no more that 27% of the total reaction mixture is comprised of $C_8$ alkylation or less, and no more than 15% of the total reaction mixture is comprised of $C_{24}$ alkylation or more.

3. The alkylated diphenylamine of claim 1 wherein the isobutylene oligomer has a number average molecular weight of about 120 to about 600 and a methylvinylidene content of at least about 25%.

4. A composition comprising:
A) an organic product selected from the group consisting of lubricants, hydraulic fluids, metal-working fluids, fuels, and polymers; and
B) a stabilizing amount of an alkylated diphenylamine of the general formula:

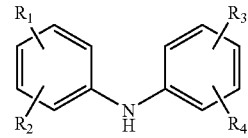

wherein $R_1$, $R_2$, $R_3$, and $R_4$ are independently selected from the group consisting of hydrogen, oligomers of isobutylene, and oligomers of propylene, provided that at least one of $R_1$, $R_2$, $R_3$, and $R_4$ is not hydrogen, prepared by a process comprising adding to a diphenylamine a mixture of oligomers of isobutylene or a mixture of oligomers of propylene in which said mixtures comprise highly reactive fractions, as well as fractions having lesser reactivity, in the presence of an acidic clay catalyst at a temperature low enough to prevent substantial deactivation of the catalyst until the addition is complete and then increasing the temperature to increase the alkylation rate of the less reactive fractions to yield a product that comprises 0.1 to 1% diphenylamine, <10% tert-butyl diphenylamine, <10% di-tert-butyl diphenylamine, <10% mono-octyl diphenylamine, >20% dodecyl diphenylamine, >15% hexadecyl diphenylamine, <10% eicosenyl diphenylamine, <7% tetracosenyl diphenylamine, <4% octacosenyl diphenylamine and <2% polyisobutyl diphenylamine.

5. The composition of claim 4 wherein no more that 27% of the total reaction mixture of the alkylated diphenylamine is comprised of $C_8$ alkylation or less, and no more than 15% of the total reaction mixture is comprised of $C_{24}$ alkylation or more.

6. The composition of claim 4 wherein the isobutylene oligomer that is added to the diphenylamine has a number average molecular weight of about 120 to about 600 and a methylvinylidene content of at least about 25%.

7. The composition of claim 4 wherein the alkylated diphenylamine is present in concentrations of from about 0.05 to about 10.0% by weight based on the material to be stabilized.

8. The composition of claim 4 wherein the organic product is a lubricating oil.

9. The composition of claim 4 wherein the organic product is an elastomer.

* * * * *